United States Patent [19]

Jones et al.

[11] 4,164,140

[45] Aug. 14, 1979

[54] METHOD AND APPARATUS FOR MEASURING MATERIAL PROPERTIES RELATED TO STRENGTH

[75] Inventors: Brenton E. Jones; Robert E. Reusser, both of Bartlesville, Okla.

[73] Assignee: Phillips Petroleum Company, Bartlesville, Okla.

[21] Appl. No.: 873,645

[22] Filed: Jan. 30, 1978

[51] Int. Cl.² .............................................. G01N 3/24
[52] U.S. Cl. ......................................... 73/54; 73/845
[58] Field of Search ................... 73/88 R, 54, 58, 150, 73/59, 53, 64.1

[56] References Cited

U.S. PATENT DOCUMENTS

| | | | |
|---|---|---|---|
| 1,225,438 | 5/1917 | Howard | 73/54 X |
| 1,745,714 | 2/1930 | Reynolds et al. | 73/228 X |
| 2,045,813 | 6/1936 | Waterbury | 177/263 X |
| 2,865,197 | 12/1958 | Penther et al. | 73/58 |

*Primary Examiner*—Jerry W. Myracle

[57] ABSTRACT

Material properties related to strength are measured, using a force measuring device in cooperation with a testing device which is placed in contact with the material being measured while the material being measured is in a molten state, the testing device being such that the molten material can flow through at least a part of the testing device.

14 Claims, 4 Drawing Figures

METHOD AND APPARATUS FOR MEASURING MATERIAL PROPERTIES RELATED TO STRENGTH

FIELD OF THE INVENTION

This invention relates in one aspect to a method for measuring material properties related to strength. In another aspect, it relates to an apparatus suitable for performing the measurement.

BACKGROUND OF THE INVENTION

Often it is necessary to be able to measure the strength properties of materials. For example, in the fabrication of rubberized asphalt, the selection of the type and amount of rubbery material to be used in the asphalt will alter various strength properties of the asphalt, for example, the force required to pull the asphalt mass apart and the persistence of this force. These properties are related to toughness and tenacity (described below).

Asphalt, because of its availability, low cost, and ease of handling is a valuable base material for a wide variety of uses ranging from asphaltic concrete paving, sealants and adhesives to roofing and pond membranes, mastics and coatings. Although quite versatile in its application areas, it is, nevertheless, deficient in certain performance properties such as flexibility at low temperatures and toughness at elevated temperatures. To improve these properties as well as impart additional flexibility, elasticity, water resistance, etc., certain thermoplastic type polymeric modifying materials such as synthetic rubber have been added to the base asphalt. Often these materials are added in the range of 0.5 to 10 weight percent of the base asphalt. The selection of the exact rubbery material to be used to obtain the desired properties for a particular application is one that requires very carefully controlled laboratory tests and examinations.

When selected rubbery materials and asphalt are combined, nearly every important physical property of the asphalt is altered to some degree. The most prominent effect to be noted is the force required to pull apart masses of rubberized asphalt and particularly, the persistence of this force over long extensions.

A simple test, referred to as the Benson Test Method, has been used to measure these properties in asphalt but its usefulness is limited by the adhesive bond strength between the test measuring apparatus and the asphalt. In making the test, a small (1.905 cm, 0.75 in diameter) hemispherical metal head is lowered into a molten sample of asphalt to be tested, the head being lowered sufficiently to bring substantially the entire hemispherical surface in contact with the sample but not so far that the asphalt covers the head. The sample is then cooled to a desired temperature, and the force required to remove the head is recorded. The Benson Test Method is described in Roads and Streets, April 1955, pg. 138 and Roads and Engineering Construction, August 1955, pg. 78. The test, however, is limited to asphalt compositions containing less than about 2 or 3 weight percent rubber because at about that point, the cohesive strength of the asphaltic composition begins to exceed its adhesion to the metal head. Hence, there exists a need for some type apparatus or test method to accurately measure toughness and tenacity of asphaltic compositions containing more than about 2 or 3 weight percent rubber.

It is an object of this invention to measure strength properties of various materials. Another object of this invention is to provide a test apparatus for such measurement.

STATEMENT OF THE INVENTION

According to the invention, strength properties of materials are measured by placing a testing device in contact with the material while the test material is in a molten state, the testing device having a shape through at least a part of which the molten test material can flow and the testing device having associated therewith a force measuring device, and then measuring the force required to pull the testing device from the material. In one embodiment, a testing apparatus which contains a mesh is provided.

PREFERRED EMBODIMENTS OF THE INVENTION

In the practice of the invention, the testing apparatus can be any shape through at least a part of which molten material can pass. For example, a screen or a mesh formed into any suitable shape, a corkscrew shape, or a hand- or claw-like shape can be used. The overall shape of the testing device is not important, so long as the molten material can flow into and around the openings in the testing apparatus, and so long as the shape of the testing apparatus is not substantially altered as the apparatus is being pulled from the material being tested. However, a shape having a large number of openings (for example, a screen or mesh) is preferred because the large number of openings through which the molten material can flow permit very good contact between the testing device and the material being measured. The screen mesh size should be any size that permits easy flow of the hot, molten material being tested through the screen or mesh. For example, a screen mesh size of 5 to 20 is suitable for hot asphalt compositions.

The overall size of the testing device is not believed to be important so long as it is compatible with the force measuring device used and with the amount of material being tested. However, since the measurement being made is the actual force required to move the testing device relative to the molten material, it is clear that the numerical measure obtained is affected by the size and shape of the device. For qualitative comparisons between samples this is sufficient, provided, of course, that the same device is used for all tests of a comparative series. For long term use in a particular technology or industry one should provide for the use of standardized testing devices and conditions.

The material used to construct the testing device (which comes in contact with the hot, molten material being tested) should be such that it will remain essentially rigid and undistorted throughout the test. Therefore, the softening point of the materials used to construct the testing device should be higher than the highest temperature to which the testing device is subjected. The material which is used to construct the testing device is also required to be such that it does not chemically or in any other way interfere with the integrity of the material being measured. For example, when the material being measured is rubberized asphalt, aluminum, carbon steel, stainless steel, brass, copper, or mixtures thereof would be suitable in this invention.

Figure 1:
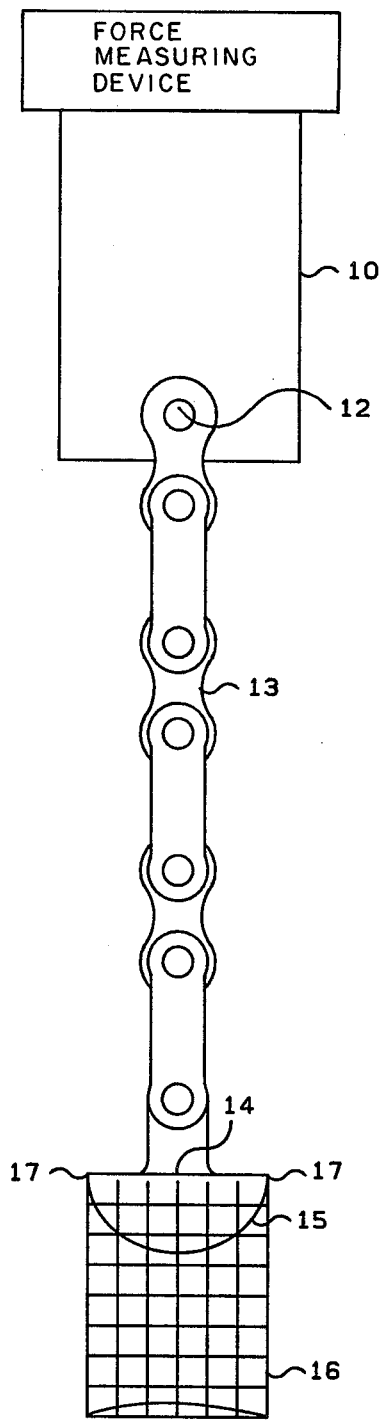
FIG. 1 is an elevation of an embodiment of the testing device provided in the invention.

Referring to the drawing, FIG. 1 shows the embodiment of the apparatus which was used in Example II. This embodiment features a flat, rectangular metal plate 10, to which a force measuring device such as an Instron Test Machine (not shown) can be attached and to which is welded at point 12 a flexible metal chain 13. Flexible metal chain 13 is welded at its lower end at area 14 to solid, metal hemisphere 15. Cylindrical metal screen 16 is welded to the circumference of solid metal hemisphere 15, (the extremities of which are shown at points 17), whereas the bottom edge of cylindrical metal screen 16 is open. Thus, in this embodiment, the testing device (which is placed in contact with the molten test material) comprises metal hemisphere 15 and cylindrical metal screen 16; and the means for associating the testing device with a force measuring device (not shown) is flexible metal chain 13 and metal plate 10.

The testing device must be suitably connected to a force measuring device so that the force required to withdraw the testing device from the molten material can be measured. Although, in FIG. 1, a metal plate 10 and a flexible metal chain 13 connect the force measuring device with the testing device, any suitable type of connecting means which will not be essentially elongated upon withdrawal of the testing device from the material being tested can be used. If desired, for convenience in use of a force measuring instrument such as an Instron Test Machine, the connecting means can have one or more links (as does flexible metal chain 13 shown in FIG. 1). It is important, however, that the part of the test apparatus which is placed in contact with the molten material is the same for all tests in which the device is used. In this way, the variations in the test results will be due only to the differences in the materials being tested.

In the practice of the invention, the above-described apparatus is used to measure strength properties of materials in the following way. The testing device (which contains openings through which the molten material to be measured can flow) is placed in contact with the molten material. It is within the scope of this invention to insert the testing device into the molten material; it is equally within the scope of this invention to pour the molten material over the testing device, thereby covering it. As stated above, in order to compare results obtained in various runs through use of the testing device, it is important that in all such runs which are to be compared, the only differences in the results be due to differences in the materials being tested. Therefore, although the testing device can be used in a variety of ways, in order to have meaningful comparisons of results, the same procedure should be used with all materials which are tested for a particular use.

Once the testing device has been placed in contact with the molten material which is being tested, the device can be pulled out of the material being tested at any desired time thereafter; and the force required to pull the testing device from the material can be measured. The force required to remove the test apparatus from the molten test material can be investigated at any desired temperature, provided that the test apparatus sustains the forces being applied without being essentially distorted.

Although the method and apparatus according to the invention are particularly useful in determining strength properties of rubberized asphaltic compositions (for example, the toughness and tenacity thereof), the method and apparatus according to the invention are not limited to use with such materials. Rather, it is expected that the method and apparatus according to the invention will be useful for measuring strength properties of any material which is soft enough at the desired test temperature to allow removal of the embedded portion of the test apparatus without physical distortion or injury to the apparatus. Thermoplastic materials (i.e., materials which are capable of being repeatedly softened by heat and hardened by cooling) are particularly amenable to measurement with the method and device according to the present invention. These include, for example, asphalts, conjugated diene-based polymers, monovinyl aromatic-based polymers, copolymers and terpolymers of conjugated dienes and monovinyl aromatics, polyolefins, polyvinyl chlorides, polyesters, and mixtures thereof.

Figure 2A:
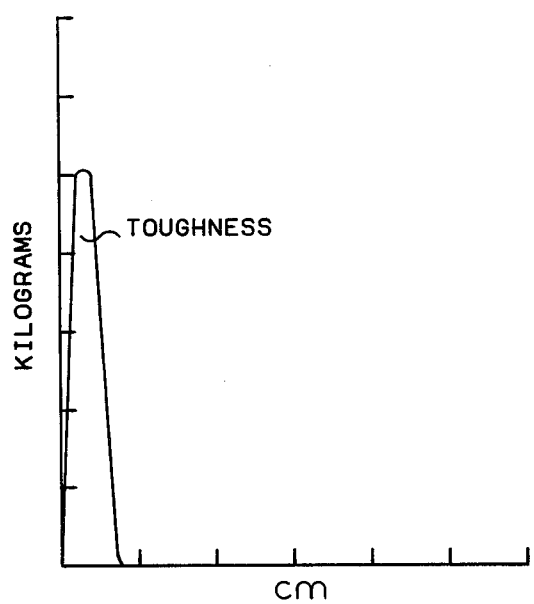
FIGS. 2A and 2B are graphical representations of toughness and tenacity of a particular asphalt, before and after rubberization.
Figure 2B:
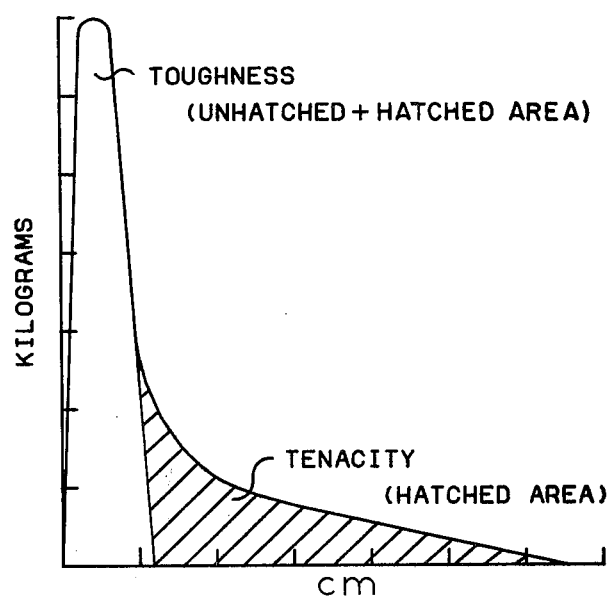

When asphalt is tested by embedding a test apparatus in the material being tested and then measuring the force required to withdraw the test apparatus at a constant speed, a certain maximum force or peak load is quickly reached, after which, with continuing movement, the force rapidly decreases to zero, as shown in FIG. 2A. However, as shown in FIG. 2B, when the same asphalt is effectively rubberized and tested under the same conditions, a somewhat greater peak load is attained and in addition, the force curve does not immediately drop to zero, but continues over a long distance with an appreciable load. To describe these strength-related behaviors, the terms "toughness" and "tenacity" have been adopted.

The toughness of an unrubberized asphalt is calculated from the entire area under the stress-strain curve, (see FIG. 2A) expressed in kilogram-centimeters of work. There is little, if any, tenacity in an unrubberized asphalt (see FIG. 2A).

The tenacity of a rubberized material is calculated from the cross-hatched area under the curve, (see FIG. 2B). It is determined by tangentially extending the curve descending from the peak load condition, to the zero force axis. For a rubberized asphalt, toughness is calculated from the entire area under the curve, (see FIG. 2B).

Both toughness and tenacity are calculated by the following formula:

$$T = \frac{\text{Instron Cross-Head Speed}}{\text{Instron Chart Speed}} \times A \times a$$

where:
T = Tenacity or Toughness in kg-cm
A = Appropriate area in kg-cm
a = Instron recorder attenuation

EXAMPLES

In the following examples, the strength properties of toughness and tenacity of various rubberized asphalt compositions were tested both with the prior art Benson Head apparatus (as described above) and with the method and apparatus according to the invention. Duplicate samples of each rubberized asphalt were made, one of which duplicates was tested with the Benson Head apparatus described above, and the other of which duplicates was tested with the apparatus according to the invention. The method of insertion and removal of each apparatus was kept as nearly alike as possible. The embodiment of the inventive testing device and means of connection to the force measuring device used (illustrated in FIG. 1) were identical to the Benson Head apparatus and means of connection to the force measuring device used in the control runs, with one essential difference. That difference is that the embodiment of the apparatus according to the invention had a cylindrical metal screen 16 attached to the circumference of the hemisphere 15. The cylindrical metal screen 16 had an inside diameter of 1.9 cm (0.74 in.) and a height of 2.54 cm (1.0 in.), with an approximate screen size of 10 mesh. The material from which the screen was formed was steel.

For each run, the respective test apparatus used on the asphalt composition being tested was clamped into an Instron (Model TT) testing machine; and the force required to remove the apparatus at a constant speed vertically from the material being tested at the temperature given below was recorded at a constant chart speed of 12 in. per minute and a constant cross-head speed of 10 in. per minute. The force measured in kilograms as a function of the distance of the testing device from its starting position in the test material is recorded and is plotted, providing a stress-strain curve, expressed in kilogram-centimeters of work.

In Examples I and II, copolymer A (described below) was added in various amounts to the asphalt being tested. The rubberized specimens were tested in Example I with the Benson Head apparatus and in Example II with the inventive apparatus. In Example III, butadiene/styrene copolymer-asphalt blends containing high (i.e., greater than 3) weight percent of other modifiers were prepared and tested with both the Benson Head apparatus and the apparatus according to the invention.

EXAMPLE I (Control)

Approximately 800 grams of 85–100 penetration grade asphalt was placed in an electrically heated stainless steel beaker and heated to 191° C. (375° F.) with a 3-bladed "bolt-prop" type propeller with diameter of 5.08 cm (2 in.). To the hot asphalt was slowly added 24.7 grams of crumb grade radial teleblock copolymer (referred to as copolymer A), having a weight ratio of 70:30 butadiene:styrene and a weight average molecular weight ($M_w$) of 300,000. The mixture was continuously stirred and heated at 177° C. for two hours, although homogeneity was achieved in less time. A portion (108 ml) of the hot blend was poured into a six ounce round can (6.98 cm diameter × 5.08 cm height) having a total capacity of 130 ml. The Benson Head test apparatus was lowered into the center of the hot mix so that the flat surface of the hemispherical apparatus was level with the surface of the hot rubberized asphalt mix. The apparatus and hot asphalt mix were held stationary while the total mass was cooled to 25° C. (77° F.), after which the hemispherical test apparatus was removed vertically from the cooled rubberized asphalt mix by means of an Instron Test Machine (Model TT). The area under the stress-strain curve was measured in kilogram-centimeters. Using the equation and the appropriate portion of the stress-strain curve (described above), the toughness of this material was calculated to be 91.4 kilogram-centimeters. Using the same equation, tenacity was calculated from the appropriate portion of the stress-strain curve (described above) to be 68.2 kilogram-centimeters.

Other runs were made, using other amounts of copolymer A shown in Table I; and the tenacity and toughness of these samples were calculated. The results are shown in Table I.

Table I

| Toughness and Tenacity of Rubberized Asphalt Determined by Control Benson Head Test Apparatus | | |
|---|---|---|
| (85–100 Pen Asphalt) | | |
| Wt. % Copolymer A | Toughness, kg-cm | Tenacity, kg-cm |
| 0 | 12.8 | 3.2 |
| 3 | 91.4 | 68.2 |
| 7 | 96.8 | 80.9 |
| 10 | 36.9 | 11.1 |

EXAMPLE II (Invention)

Another portion (108 ml) of hot rubberized asphalt containing 3 weight percent of copolymer A as described above was poured into a six ounce round can which was essentially identical to that described in Example I. The inventive apparatus was then lowered into the hot asphalt mixture so that the top of the cylindrical metal screen 16 in FIG. 1 was level with the surface of the hot rubberized asphalt mix. The apparatus and asphalt mix was cooled and tested in the same manner as described in Example I. Next, runs were made using other amounts of copolymer A; and toughness and tenacity were determined for these samples. The results are shown in Table II.

Table II

| Toughness and Tenacity of Rubberized Asphalt Determined by Inventive Screen-Type Apparatus | | |
|---|---|---|
| (85–100 Pen Asphalt) | | |
| Wt. % Copolymer A | Toughness, kg-cm | Tenacity, kg-cm |
| 0 | 87.2 | 13.5 |
| 3 | 371.5 | 215.9 |
| 7 | 986.1 | 889.1 |
| 10 | 1,360.5 | 1,267.7 |

The results shown in Tables I and II (which are dramatically illustrated in FIG. 3) clearly demonstrate that the inventive test apparatus provides a measure of toughness and tenacity which is much more useful in characterizing a composition than is the measure of toughness and tenacity obtained by using the Benson Head apparatus. From FIG. 3, it can clearly be seen that for 0 to about 3 weight percent polymer A, both the Benson Head apparatus and the apparatus according to the invention give values of toughness and tenacity, each of which corresponds to one and only one weight percent of polymer A. However, above about 3 weight percent of polymer A, the graphs of toughness and tenacity for the two types of apparatus are clearly very different. Because the slopes of the graphs of toughness and tenacity for the apparatus according to the invention remain positive, it can be seen that the apparatus according to the invention is useful for characterizing the material being measured with regard to its toughness and tenacity. In fact, from such a graph, one could predict what tenacity and toughness a rubberized asphalt containing a particular weight percentage of polymer A would have.

Figure 3:
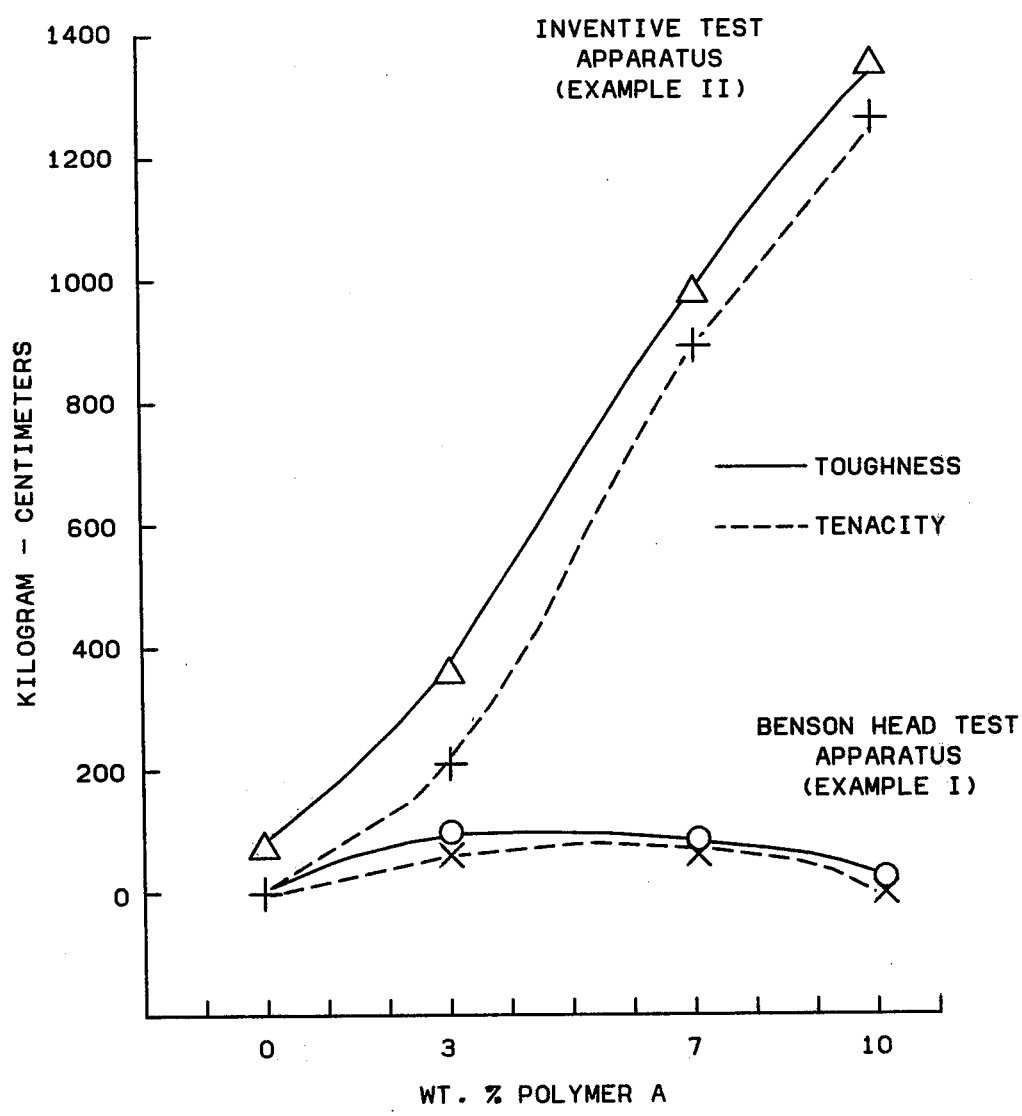
FIG. 3 is a graphical representation of toughness and tenacity values of a particular rubberized asphalt, the values obtained by using the Benson Head Test Apparatus (further discussed in Example I) and by using the Inventive Test Apparatus (further discussed in Example II).

On the other hand, as shown in FIG. 3, the Benson Head apparatus gives a graph of toughness and tenacity which has first a positive slope, then zero slope, and then a negative slope. This graph demonstrates that the Benson Head apparatus is *not* useful for rubberized asphalt mixes containing greater than about 3 weight percent of modifying polymer A because one value of toughness does not correspond to a single weight percent of polymer. Therefore, the Benson Head apparatus is not useful for characterizing such rubberized asphalt mixes since that apparatus tells substantially nothing about the strength or character of the composition, corresponding to the fact that the Benson Head actually pulls loose from the rubberized asphalt before a meaningful value of toughness and tenacity can be measured.

EXAMPLE III

Other butadiene/styrene copolymer-asphalt blends were prepared and tested as described above, the only difference from the procedure of Examples I and II being that the weight ratio of butadiene to styrene was increased in two runs above the weight ratio used in Examples I and II; and a run with butadiene and isoprene was made with various weight percents in this particular copolymer added to the asphalt. A summary of these additional runs is shown in Table III.

Table III

Comparison of Tenacity-Toughness Values Determined by Two Test Apparatuses

| | Wt. % Copolymer | Benson Heat Apparatus | | Inventive Apparatus | |
|---|---|---|---|---|---|
| | | Toughness$^a$ | Tenacity$^a$ | Toughness$^a$ | Tenacity$^a$ |
| 1. | 0 | 12.8 | 3.2 | 87.2 | 13.5 |
| 2. | 85 I/15S$^b$ | | | | |
| | 3 | 67.3 | 25.7 | 331.9 | 208.2 |
| | 7 | 58.7 37.2 | 432.9 | 250.2 | |
| | 10 | 61.0 | 36.3 | 485.0 | 365.6 |
| 3. | 75 Bd/25S$^c$ | | | | |
| | 3 | 52.2 | 25.9 | 143.2 | 43.9 |
| | 7 | 17.6 | 9.8 | 123.3 | 44.3 |
| | 10 | 13.6 | 9.4 | 77.8 | 56.7 |
| 4. | 60 Bd/40S$^d$ | | | | |
| | 3 | 30.6 | 4.5 | 113.7 | 19.8 |
| | 7 | 74.4 | 17.3 | 359.0 | 188.0 |
| | 10 | 72.6 | 34.3 | 572.8 | 432.5 |

$^a$Units in kilogram-centimeters.
$^b$I is isoprene, radial teleblock copolymer, $M_w$ 300,000.
$^c$Linear block copolymer, $M_w$ 83,000.
$^d$Radial teleblock copolymer, $M_w$ 150,000.

The results in Table III further illustrate the superiority of the inventive apparatus over the prior art Benson Head apparatus when both are used to measure toughness and tenacity of asphalt compositions containing greater than 3 weight percent modifier levels.

This invention is intended to cover reasonable additions and modifications which would be apparent to one having ordinary skill in the art.

We claim:

1. A method for measuring strength properties of a material, the improvement comprising:
   (a) placing a testing device in contact with said material when said material is in a molten state, said testing device
      1. being essentially nondistortable during the test;
      2. having a shape through at least a part of which said molten material can flow; and
      3. having means for associating therewith a force measuring device; and
   (b) measuring the force required to pull said testing device from said material.

2. A method according to claim 1 wherein said testing device is rigid and stays rigid while it is being pulled from said material and wherein said testing device is made from a material having a softening point that is higher than the temperature of said molten material.

3. A method according to claim 2, wherein said testing device is pulled from said material after said material has cooled below the temperature it had when said testing device was placed in contact with said molten material.

4. A method according to claim 3 wherein said testing device comprises a screen.

5. A method according to claim 4 wherein said testing device is inserted into said molten material.

6. A method according to claim 5 wherein said material being tested is a thermoplastic material and wherein said method includes also the step of measuring the force required to remove said testing device at a constant speed from said material being tested, said force being measured as said testing device is continuously removed from a plurality of positions within said material being tested.

7. A method according to claim 6 wherein said material being tested is rubberized asphalt.

8. A method according to claim 1 wherein said element is vertically inserted into said molten material and is later vertically removed from said material.

9. An apparatus for measuring strength properties of a test material, said apparatus comprising:
   (a) an element to be placed in contact with said test material while said test material is in a molten state, said element
      1. comprising a screen in the shape of a cylinder, the bottom of said cylinder being open,
      2. being essentially nondistortable during the test, and
      3. having a means of attachment to which a force measuring device can be attached; and
   (b) a force measuring device operable in combination with said element.

10. An apparatus according to claim 8 wherein said test element comprises a hemisphere attached to said cylindrical screen.

11. An apparatus according to claim 10 wherein said cylindrical screen is made of metal.

12. An apparatus for measuring strength properties of a test material, said apparatus comprising:
   (a) an alement to be placed in contact with said test material while said test material is in a molten state, said element
      1. comprising a metal cylindrical screen attached to a hemisphere,
      2. being essentially nondistortable during the test, and
      3. having a means of attachment to which a force measuring device can be attached; and
   (b) a force measuring device operable in combination with said element.

13. An apparatus to be used with a force measuring device for measuring strength properties of a material, said apparatus to be placed in contact with a test material while said test material is in a molten state, said element comprising:
   (a) a hemisphere; and
   (b) a cylindrical screen which is attached to the circumference of the outside of said hemisphere.

14. An apparatus according to claim 13 wherein said hemisphere and said cylindrical screen are metal.

* * * * *

UNITED STATES PATENT AND TRADEMARK OFFICE
CERTIFICATE OF CORRECTION

PATENT NO. : 4,164,140

DATED : August 14, 1979

INVENTOR(S) : Brenton E. Jones and Robert E. Reusser

It is certified that error appears in the above-identified patent and that said Letters Patent are hereby corrected as shown below:

Column 8, line 41 (claim 10, first line), "8" should read --- 9 ---.

Signed and Sealed this

Sixth Day of November 1979

[SEAL]

Attest:

RUTH C. MASON
Attesting Officer

LUTRELLE F. PARKER
Acting Commissioner of Patents and Trademarks